United States Patent [19]

Schinzel et al.

[11] Patent Number: 4,587,338

[45] Date of Patent: May 6, 1986

[54] PERFLUOROALKYL ESTERS OF ANTHRANILIC ACIDS

[75] Inventors: Erich Schinzel, Hofheim am Taunus; Manfred Pelster, Speyer, both of Fed. Rep. of Germany

[73] Assignee: Hoechst Aktiengesellschaft, Fed. Rep. of Germany

[21] Appl. No.: 650,357

[22] Filed: Sep. 13, 1984

[30] Foreign Application Priority Data

Sep. 16, 1983 [DE] Fed. Rep. of Germany ....... 3333457

[51] Int. Cl.⁴ ................. C07D 251/42; C07D 251/50; C07D 251/70; C07D 251/44
[52] U.S. Cl. .................................. 544/197; 544/198; 544/208; 544/209; 544/211; 544/212; 260/239.7
[58] Field of Search ............... 544/197, 198, 208, 209, 544/211, 212; 260/239.7

[56] References Cited

U.S. PATENT DOCUMENTS

| | | | |
|---|---|---|---|
| 3,278,253 | 10/1966 | Weckler et al. | 544/197 |
| 3,400,121 | 9/1968 | Weckler et al. | 544/197 |
| 3,697,520 | 10/1972 | Winter | 544/197 |
| 4,183,929 | 1/1980 | Conrow | 544/197 |

Primary Examiner—John M. Ford
Attorney, Agent, or Firm—Connolly and Hutz

[57] ABSTRACT

Perfluoroalkyl esters of anthranilic acids, of the formula (1)

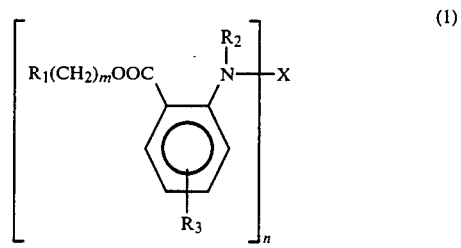

in which $R_1$ is perfluoroalkyl or perfluoroalkoxy-perfluoroalkyl, $R_2$ is hydrogen, alkyl or phenyl, $R_3$ is one or more non-chromophoric radicals, such as fluorine, chlorine, bromine, lower alkyl, lower alkoxy, acylamino, carboxyl or functionally modified carboxyl groups, sulfo or functionally modified sulfo groups, or phenyl, X is the radical of an aliphatic or aromatic monocarboxylic or polycarboxylic acid, the radical of a halogen-active heterocyclic compound or an alkylaminocarbonyl or arylaminocarbonyl radical, m is an integer from 1 to 6, preferably 1 to 4 and n is an integer from 1 to 3. These compounds are useful for soil-repellent finishing of textile material.

5 Claims, No Drawings

PERFLUOROALKYL ESTERS OF ANTHRANILIC ACIDS

The invention relates to novel perfluoroalkyl compounds which are useful for the soil-repellent finishing of fibers or fabrics of synthetic, semi-synthetic or natural materials, preferably of polyethylene terephthalate or polyamides.

Compounds which contain perfluoroalkyl radicals are already known as soil-repellent agents. Thus, DE-OS No. 2,628,776 describes compounds which essentially consist of one or more fluorinated compounds having one or more benzene rings. Further, soil-repellent agents composed of polymeric compounds containing fluorinated groups are known. Specifically, fluorinated compounds are described in U.S. Pat. No. 3,547,861, which relates to fluorinated acrylates and polyacrylates, the fluorinated radical being derived from a fluorinated alcohol having a terminal fluorinated alkoxy group. Similar products for such uses, wherein the fluorinated radical of the polyacrylate is a straight-chain fluorinated alcohol, are also known.

The compounds according to the invention correspond to the general formula (1)

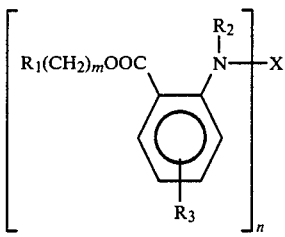
(1)

in which $R_1$ is perfluoroalkyl or perfluoroalkoxy-perfluoroalkyl, in each case having a total of 2–20, preferably 4–14, carbon atoms, $R_2$ is hydrogen, straight-chain or branched $C_1$–$C_4$-alkyl or phenyl, $R_3$ is one or more non-chromophoric radicals from the group comprising fluorine, chlorine, bromine, lower alkyl, lower alkoxy, acylamino, carboxyl or functionally modified carboxyl groups, sulfo or functionally modified sulfo groups, or phenyl, X is the radical of an aliphatic or aromatic monocarboxylic or polycarboxylic acid, the radical of a halogen-active heterocyclic compound or an alkylaminocarbonyl or arylaminocarbonyl radical, m is an integer from 1 to 6, preferably 1 to 4 and n is an integer from 1 to 3.

Preferred perfluoroalkyl compounds of the formula (1) are those in which $R_1$ is a group of the formula $C_lF_{2l+1}$—, a group of the formula $H(C_2F_4)_o$— or a group of the formula $(CF_3)_2CFO(CF_2)_p$—, l is 6, 8, 10, 12 or 14, o is 1, 2, 3 and 4 and p is an integer from 2 to 8, $R_2$ is hydrogen, methyl, ethyl or phenyl, $R_3$ is one or more radicals from the group comprising chlorine, methyl, methoxy, —COOH, —COOCH$_3$, —SO$_3$H, —SO$_2$OC$_6$H$_5$, —SO$_2$NH$_2$, cyano or phenyl, X, if n=1, is a group of the formula —CO—(NH)$_a$—Y or

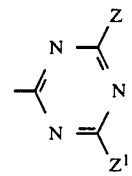

if n=2, is a group of the formula —CO—, —CO—(NH)$_a$—Y'—(NH)$_a$—CO— or

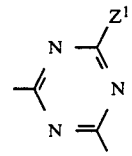

and, if n=3, is a group of the formula a is 0 or 1, Y is alkyl, alkoxy, phenyl, chlorophenyl or alkylphenyl, Y' is alkylene, phenylene, chlorophenylene, alkylphenylene, dicyclohexylmethane or, if a=0, is a direct bond, Z is chlorine, hydroxyethylamino or bis-hydroxyethylamino, and $Z^1$ is chlorine, hydroxyethylamino, bis-hydroxyethylamio, dialkylaminoalkylamino, trialkylammoniumalkylamino, sulfoethylamino, N-alkyl-N-sulfoethylamino, piperazinyl, N-hydroxyethylpiperazinyl, N-methyl-N-hydroxyethylpiperazinyl, phenylamino, sulfophenylamino, disulfophenylamino, alkylphenylamino or sulfatoethylsulfonylphenylamino.

The term "perfluoroalkyl" or "perfluoroalkoxy" comprises both groups with terminal —CF$_3$ and those with terminal —CF$_2$H groups. The terms "functionally modified carboxyl groups" and "functionally modified sulfo groups" comprise cyano, carboxylic acid ester, carboxamide, monoalkylcarboxamide and dialkylcarboxamide groups, and sulfonic acid ester, sulfonamide, monoalkylsulfonamide and dialkylsulfonamide groups, respectively. Alkyl and alkoxy groups, unless defined otherwise, contain 1 to 4 carbon atoms. An acyl group is essentially to be understood as a $C_1$–$C_4$-alkanoyl group. The carboxyl groups and sulfo groups can also be present in the form of salts with colorless cations, for example as ammonium, potassium or sodium salts.

The perfluoroalkyl esters of anthranilic acids according to the invention are soil-repellent compounds which possess high repellency towards water and oil and which remain on the fiber even after repeated washing and dry cleaning. A further advantage of the compounds according to the invention is that they can be applied to the fiber materials in solution or as a dispersion or can be incorporated by mixing with pellets of the thermoplastic and subsequent shaping to form fibers or filaments. A further special advantage of the novel soil-repellent agents is that they permit perfectly satisfactory dyeing of the fibers or filaments into which these agents are incorporated. The novel soil-repellent agents can also be satisfactorily applied from a bath, together with a dyestuff.

The compounds (1) according to the invention are prepared by reacting isatoic anhydrides (2) with perfluoroalkyl alcohols or perfluoroalkoxy-perfluoroalkyl alcohols to give the o-amino-anthranilic acid esters (3), acylation of (3) with acid halides of aliphatic or aromatic monocarboxylic or polycarboxylic acids or condensation of (3) with a halogen-active, heterocyclic compound, such as, for example, cyanuric chloride, or reaction of (3) with aliphatic or aromatic monoisocyanates or diisocyanates, as illustrated by way of example in the reaction scheme below, which relates to the reaction with cyanuric chloride.

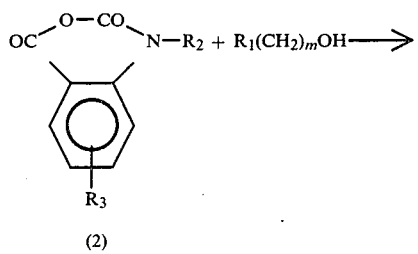

(2)

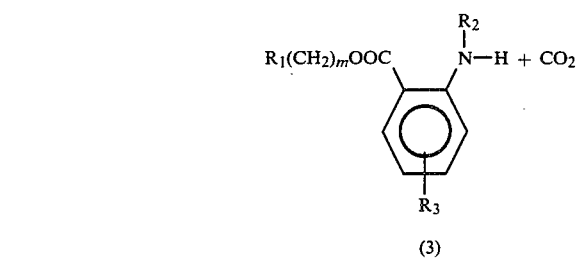

(3)

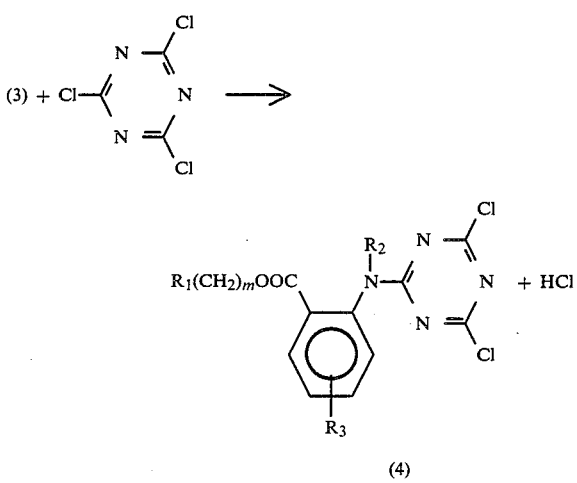

(4)

In the above formulae (2), (3) and (4), $R_1$, $R_2$, $R_3$ and m have the meaning given at the outset. The compounds stated to be preferred are prepared analogously by reaction of 1, 2 or 3 moles of the compounds of the formula (3) with compounds of the formulae $CO(Hal)_2$; Hal—CO—Y; Hal—CO—Y'—CO—Hal; OCN—Y or OCN—Y'—NCO, or with cyanuric chloride. Hal in these formulae is chlorine or bromine and the remaining symbols have the meanings given above. In the compounds of the formula (4) which are obtained by reaction of compounds of the formula (3) with cyanuric chloride, the two chlorine atoms can each individually be replaced, using conventional processes, by the radical of the anthranilic acid ester of the formula (3) or by the radical of an amine, depending on the meaning of Z and $Z^1$.

To prepare the anthranilic acid esters (3), the isatoic anhydrides (2) which have been described in several literature publications (ERDMANN, B. 32, 2164, German Pat. No. 110,577; Frdl. 5, 148) are reacted, at temperatures of up to 100° C., with an equimolecular amount of a perfluoroalkyl alcohol or perfluoroalkoxy-perfluoroalkyl alcohol at temperatures of up to 200° C. until $CO_2$ evolution has ended or, more advantageously and more gently, in the presence of alkaline catalysts, for example sodium methylate.

The acylation of the anthranilic acid esters (3) with the chlorides of aliphatic or aromatic monocarboxylic and dicarboxylic acids is carried out in organic solvents, advantageously in toluene or xylene, in the presence of a proton acceptor, for example pyridine, at temperatures of 50°–60° C.

The reaction of (3) with cyanuric chloride is advantageously carried out in ethyl acetate, without a proton acceptor, at 5°–10° C. For the further replacement of the chlorine atoms in compound (4) by the radicals of aliphatic or aromatic amines, it is advantageous to employ higher-boiling solvents, such as toluene, chlorobenzene or o-dichlorobenzene. Proton acceptors, such as pyridine or triethylamine, tend to have a disadvantageous effect on the success of these reactions.

The condensation of (3) with aliphatic or aromatic monoisocyanates or diisocyanates is advantageously carried out in polar aprotic solvents, such as dimethylformamide or N-methyl-pyrrolidone, at temperatures of 50°–60°.

Compounds which correspond to the present invention have, for example, the formulae:

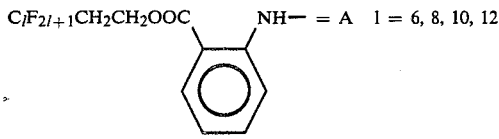

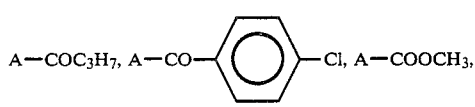

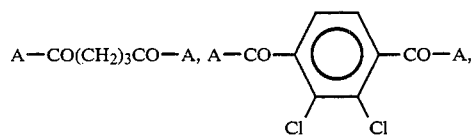

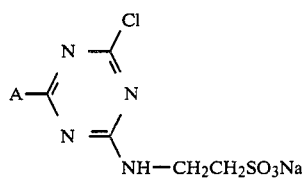

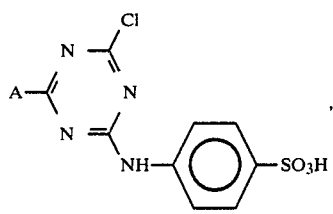
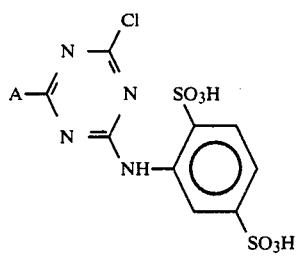
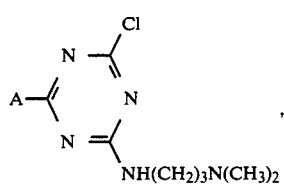
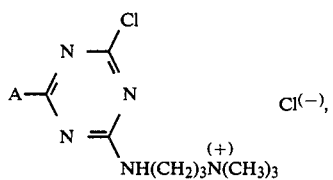
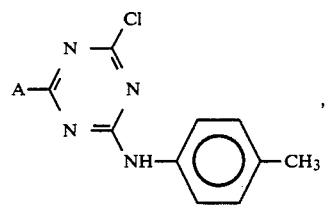
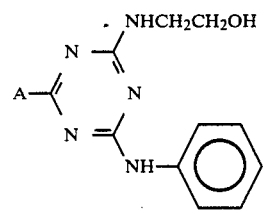
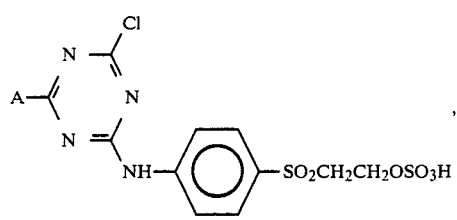
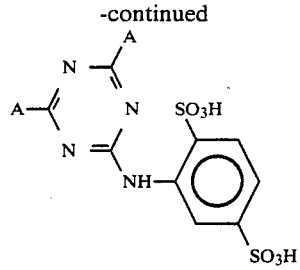
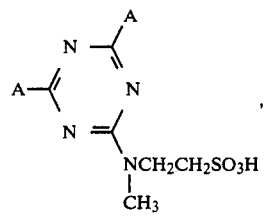
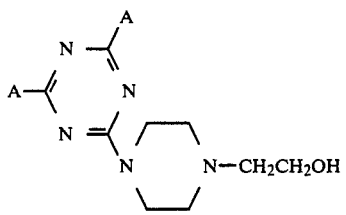
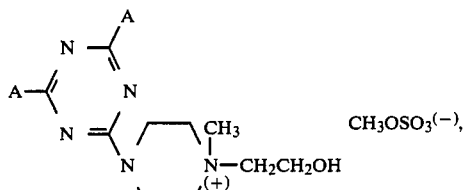
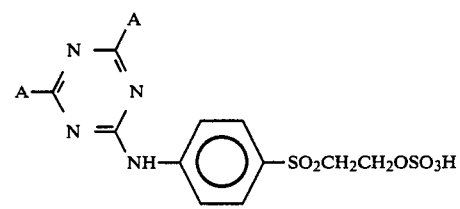
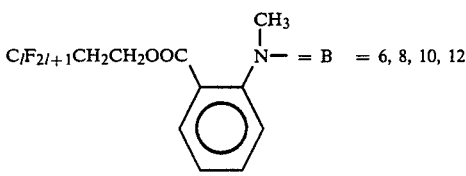
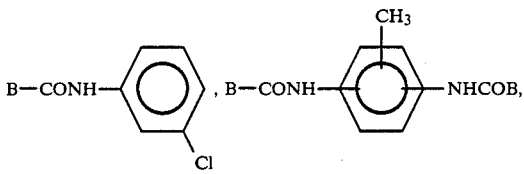
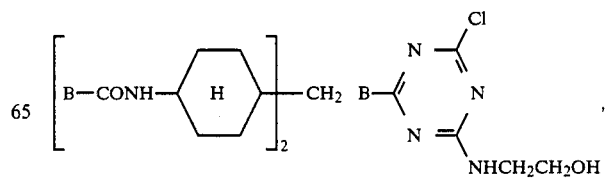

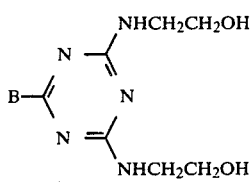

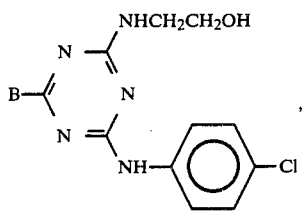

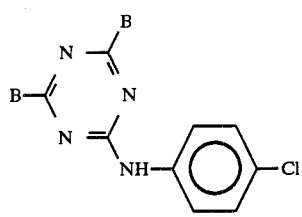

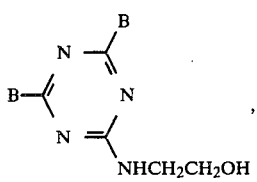

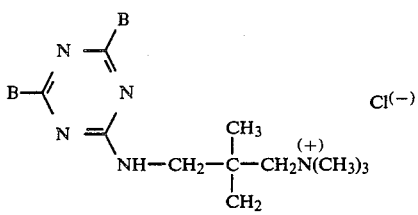

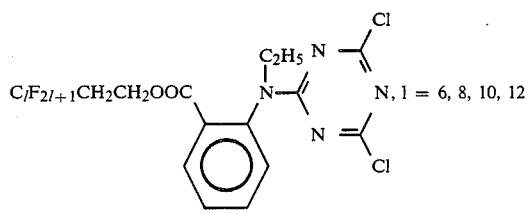

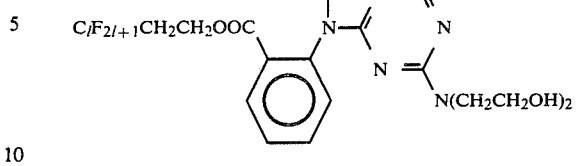

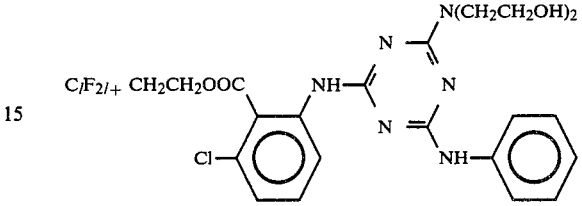

The compounds according to the invention, of the formula (1), are suitable for rendering synthetic and natural fibers and fabrics, especially polyesters, polyamide, polyacrylonitrile and wool, simultaneously hydrophobic and oleophobic. The application of these compounds to the textile material is effected according to conventional processes, by contacting a solution or dispersion of the compounds of the formula (1) indiquid medium, preferably in water or in a suitable organic solvent, by preference in acetone or dimethylformamide and then annealing the resulting textile material at elevated temperature. After having been impregnated, the textile material may be squeezed off, dried and thermofixed. It is particularly preferred to use the compounds of the formula (1) in, and conjointly with, a conventional fiber dressing. The coating of the compounds of the formula (1) on the textile material in general amounts to 0.05 to 1% by weight, expressed as content of fluorine in the compounds of the formula (1).

It is assumed that the soil-repellent properties are imparted to the thermoplastics by the present compounds of the formula (1) because of their ability to reduce the surface energy of the thermoplastics. This effect can be improved by a heat treatment at temperatures above the glass transition temperature of the thermoplastics and below the decomposition temperature of both the thermoplastics and the soil-repellent agent.

Suitable times for such a heat treatment lie in the range from about 1 to 240 minutes. The heat treatment temperatures are typically about 100° to 220° C.

A further improvement of the effect achieved with the soil-repellent agents according to the invention, which contain a hydroxyl group, is obtained by additionally using a difunctional or trifunctional epoxide or isocyanate in the liquid medium which contains the soil-repellent agent and into which the fiber or other thermoplastic article is dipped or with which these are sprayed or otherwise treated, in particular conjointly with a catalyst such as an amine in order to promote the reaction of the hydroxyl group with an epoxide group or isocyanate group during the subsequent heat treatment.

TABLE 1
Preparation examples

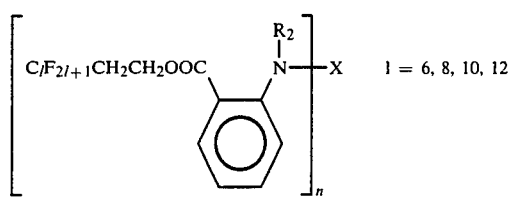 $l = 6, 8, 10, 12$

| Serial No. | $R_2$ | X | n | Method | Yield % of theory | Analysis | % F; | % Cl; | % N |
|---|---|---|---|---|---|---|---|---|---|
| (10) | H | H | 1 | A | 96.8 | calc. | 54.7; | | 2.5 |
| | | | | | | found | 53.9; | | 2.6 |
| (11) | CH₃ | H | 1 | A' | 85.3 | calc. | 53.6; | | 2.4 |
| | | | | | | found | 52.8; | | 2.6 |
| (12) | CH₃ | CH₃CO— | 1 | B | 93.1 | calc. | 49.8; | | |
| | | | | | | found | 48.9; | | |
| (13) | CH₃ | C₆H₅CO— | 1 | B' | 96.4 | calc. | 45.3; | | |
| | | | | | | found | 44.6; | | |
| (14) | CH₃ | C₂H₅OCO— | 1 | B' | 89.3 | calc. | 47.5; | | |
| | | | | | | found | 48.2; | | |
| (15) | CH₃ | —CO— | 2 | C | 89.0 | calc. | 52.2; | | |
| | | | | | | found | 51.4; | | |
| (16) | H | —COCO— | 2 | C | 84.4 | calc. | 52.4; | | |
| | | | | | | found | 51.9; | | |
| (17) | CH₃ | " | 2 | C | 81.7 | calc. | 51.0; | | |
| | | | | | | found | 51.0; | | |
| (18) | H | —CO(CH₂)₂CO— | 2 | C | 97.8 | calc. | 51.2; | | |
| | | | | | | found | 50.7; | | |
| (19) | CH₃ | —CO(CH₂)₂CO— | 2 | C | 96.7 | calc. | 50.1 | | |
| | | | | | | found | 49.2 | | |
| (20) | H | —CO(CH₂)₄CO— | 2 | C | 96.3 | calc. | 50.1 | | |
| | | | | | | found | 49.8 | | |
| (21) | CH₃ | " | 2 | C | 97.3 | calc. | 48.8 | | |
| | | | | | | found | 47.9 | | |
| (22) | H | —CO—C₆H₄—CO— (meta) | 2 | C | 96.8 | calc. | 49.3 | | |
| | | | | | | found | 48.8 | | |
| (23) | CH₃ | " | 2 | C | 97.6 | calc. | 48.0 | | |
| | | | | | | found | 47.5 | | |
| (24) | CH₃ | —CO—C₆H₄—CO— (para) | 2 | C | 97.3 | calc. | 48.0 | | |
| | | | | | | found | 47.6 | | |
| (25) | H | —CONH—C₆H₅ | 1 | D | 98.7 | calc. | 45.4 | | |
| | | | | | | found | 44.4 | | |
| (26) | H | —CONH—C₆H₄—Cl | 1 | D | 100 | calc. | 43.3 | | |
| | | | | | | found | 43.5 | | |
| (27) | H | —CONH(CH₂)₆NHCO— | 2 | D' | 100 | calc. | 48.2 | | |
| | | | | | | found | 47.8 | | |
| (28) | H | —COHN—C₆H₃(CH₃)—NHCO— 80% 2,4- 20% 2,6- | 2 | D' | 97.7 | calc. | 47.6 | | |
| | | | | | | found | 47.0 | | |

TABLE 1-continued

Preparation examples

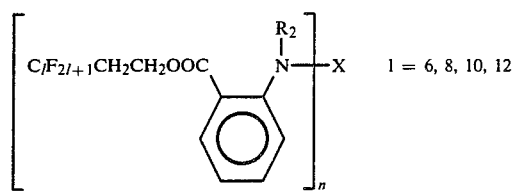

$$\left[ C_lF_{2l+1}CH_2CH_2OOC \underset{\substack{N \\ R_2}}{\overset{}{\bigcirc}} X \right]_n \quad l = 6, 8, 10, 12$$

| Serial No. | R₂ | X | n | Method | Yield % of theory | Analysis | % F; | % Cl; | % N |
|---|---|---|---|---|---|---|---|---|---|
| (29) | H | ![Cl-triazine-Cl] | 1 | E | 98.7 | calc. found | 43.6; 43.4; | 9.85; 9.8; | 7.78 7.9 |
| (30) | CH₃ | " | 1 | E | 99.6 | calc. found | 42.6; 42.2; | 9.73; 9.5; | 7.69 7.5 |
| (31) | H | ![Cl-triazine-NHPh] | 1 | F | 100 | calc. found | 40.43 40.2 | | |
| (32) | CH₃ | " | 1 | F | 92.8 | calc. found | 39.7 38.9 | | |
| (33) | H | ![Cl-triazine-N(CH₂CH₂OH)₂] | 1 | F | 90.8 | calc. found | 39.8 39.4 | | |
| (34) | CH₃ | ![Cl-triazine-N(CH₂CH₂OH)₂] | 1 | F | 95.2 | calc. found | 39.1 38.9 | | |
| (35) | H | ![N(CH₂CH₂OH)₂-triazine-N(CH₂CH₂OH)₂] | 1 | G | 64.7 | calc. found | 36.6 36.5 | | |
| (36) | CH₃ | " | 1 | G | 89.4 | calc. found | 36.0 36.3 | | |
| (37) | H | ![N(CH₂CH₂OH)₂-triazine-NHPh] | 1 | G | 70.2 | calc. found | 37.1 36.4 | | |
| (38) | CH₃ | " | 1 | G | 67.5 | calc. | 36.5 | | |

TABLE 1-continued

Preparation examples

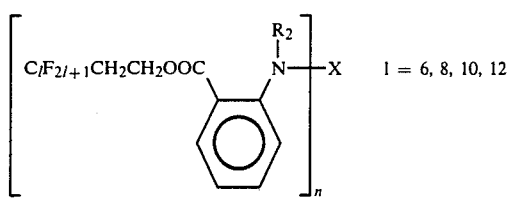

$[C_lF_{2l+1}CH_2CH_2OOC\text{-}C_6H_4\text{-}N(R_2)\text{-}X]_n$  $l = 6, 8, 10, 12$

| Serial No. | $R_2$ | X | n | Method | Yield % of theory | Analysis | % F | % Cl | % N |
|---|---|---|---|---|---|---|---|---|---|
| | | | | | | found | 35.9 | | |
| (39) | H | triazinyl-Cl | 2 | H | 97.6 | calc. found | 50.0 49.8 | | |
| (40) | $CH_3$ | triazinyl-Cl | 2 | H | 100 | calc. found | 48.9 48.1 | | 5.46 5.5 |
| (41) | H | triazinyl-$N(CH_2CH_2OH)_2$ | 2 | I | 78.3 | calc. found | 47.4 47.1 | | |
| (42) | $CH_3$ | " | 2 | I | 97.2 | calc. found | 46.5 | 46.4 | |
| (43) | H | triazinyl-NH-Ph | 2 | I | 80.5 | calc. found | 49.9 50.0 | | |
| (44) | $CH_3$ | " | 2 | I | 91.7 | calc. found | 46.9 46.3 | | |
| (45) | H | triazinyl-H | 3 | J | 90.3 | calc. found | 52.6 52.0 | | |

METHOD A 0.1 mole of sodium methylate is added to a mixture of 1 mole of the perfluoroalkylethanol $C_lF_{2l+1}CH_2CH_2OH$, $l=6, 8, 10, 12$, and 1 mole of isatoic anhydride. The reaction mixture is heated to 100°, with stirring, in the course of which a vigorous evolution of gas commences. Stirring is continued for 1 hour at 100°, the mixture is allowed to cool to room temperature and 1 liter of toluene and 50 ml of water are added. The batch is neutralized with 6 ml of glacial acetic acid, while stirring, and the aqueous phase is separated off at 40°-50°. The organic phase is additionally stirred three times with 500 ml of warm water each time, and is then dried over sodium sulfate and evaporated in vacuo. Yield: 548 g of the compound No. (10) in the form of a brownish semi-solid mass. On distillation in vacuo, a main fraction passes over at 130°-170°/0.4-1.0 mm Hg, and solidifies to a colorless mass.

METHOD A'

The procedure followed is analogous to Method A, using N-methylisatoic anhydride. When the mixture is cooled to room temperature, 7 ml of glacial acetic acid are added and thereafter the batch is distilled in vacuo. 489 g of a yellowish material pass over at 130°–170°/0.4–0.6 mm Hg and this solidifies to a glassy mass at room temperature (compound No. (11)).

METHOD B 29 g of the perfluoroalkyl N-methyl anthranilic acid ester (11) are dissolved in 150 ml of toluene and 9.4 ml of acetic anhydride and 4.8 ml of pyridine are added. The mixture is boiled for 5 hours under reflux, the solvent is evaporated off in a rotary evaporator and the yellowish oil which remains is repeatedly extracted by stirring with water at 50°. After the product has been dried at 60° in vacuo, 29.0 g of a yellow oil are obtained (compound No. (12)).

METHOD B'

Following a procedure analogous to Method B, 7.03 g of benzoyl chloride are used and the reaction mixture is finally stirred for 6 hours at 55°–60°. 33.0 g of a yellow oil are obtained (compound No. (13)).

METHOD C 0.1 mole of the anthranilic acid ester are dissolved or suspended in 350 ml of toluene and 0.05 mole of the dichloride and 0.12 mole of pyridine are added, with stirring. The mixture is heated to 55°–60° for 6–7 hours and is allowed to cool, and the reaction product which has precipitated is filtered off with suction, washed with toluene and water and dried in vacuo at 60°. If the reaction product cannot be filtered off with suction, the solvent is distilled off in vacuo and the generally resinous residue which remains is washed thoroughly with water, if appropriate while heating and with the aid of an electrically operated kneader, until a neutral reaction is obtained. The last wash water is tested for the absence of $Cl^-$ ions.

METHOD D 0.11 mole of the monoisocyanate is added dropwise to 0.1 mole of the anthranilic acid ester in 20 ml of dimethylformamide. The mixture is heated to 60°–80° C. for 3 hours, the solvent is then evaporated in vacuo and the residue is stirred for several hours with water, if appropriate after mechanical comminution. The product is filtered off with suction, washed with water and dried in vacuo at 60°.

METHOD D'

0.1 mole of the anthranilic acid ester is dissolved in 30 ml of dimethylformamide and 0.1 mole of the diisocyanate is added dropwise. The mixture is warmed to 60° and is stirred for 3 hours at this temperature. When it has cooled, the reaction mixture is poured onto 200 ml of water, the batch is stirred for several hours and the product is filtered off with suction, rinsed with water and dried at 60° in vacuo.

METHOD E 0.1 mole of the anthranilic acid ester is dissolved in 350 ml of ethyl acetate, the solution is cooled to 5°–10° and 0.1 mole of cyanuric chloride is added. The reaction mixture is stirred for 1 hour at 5°–10° and for a further 24 hours at room temperature. It is then evaporated to constant weight at 50° in a rotary evaporator. The reaction products are colorless to pale brownish powders.

METHOD F 0.1 mole of the N-(dichloro-triazinyl)-anthranilic acid ester (29) or (30) is dissolved in 350 ml of toluene at 60°–70°, 0.2 mole of an aliphatic or aromatic amine is added and the reaction mixture is stirred for 4–8 hours at 95°–100°. It is then evaporated in vacuo and the residue is twice stirred thoroughly with 350 ml of 1N hydrochloric acid. The reaction product is filtered off with suction, washed free of $Cl^-$ ions with water and dried in vacuo at 60°.

METHOD G 0.1 mole of the N-(dichlorotriazinyl)-anthranilic acid ester (29) or (30) is dissolved in 350 ml of toluene at 60°–70°, 0.2 mole of an aliphatic or aromatic amine is added and the batch is stirred for 4–8 hours at 95°–100°. 0.2–0.3 mole of the same amine or of a different aliphatic amine is then added and the reaction mixture is heated for about 65 hours to 100°. The toluene is distilled off in vacuo, the residue is repeatedly stirred thoroughly with 350 ml of 1N hydrochloric acid, if appropriate with heating, and is filtered off with suction, washed with water until free from $Cl^-$, and dried in vacuo at 60°.

METHOD H 0.1 mole of the N-(dichlorotriazinyl)-anthranilic acid ester (29) or (30) is suspended in 200 ml of toluene, 0.1 mole of the appropriate anthranilic acid ester is added and the mixture is stirred for 12 hours while boiling under reflux and while nitrogen is passed through it. The toluene is distilled off in vacuo and the residue is dried in vacuo at 50°–60°.

METHOD I 0.2 mole of an aliphatic or aromatic amine is added to 0.1 mole of the chlorotriazinyl compound (39) or (40) in 200 ml of toluene and the reaction mixture is stirred for 24 hours at the boil. The toluene is distilled off in vacuo and the residue is repeatedly stirred thoroughly with 350 ml of 1N hydrochloric acid, if appropriate while heating. The product is filtered off with suction, washed with water until free from $Cl^-$ ions and dried in vacuo at 50°–60°.

METHOD J 0.1 mole of the anthranilic acid ester (10) is added to 0.1 mole of the chlorotriazinyl compound (39) suspended in 200 ml of o-dichlorobenzene, and the mixture is stirred for a total of 36 hours, while boiling under reflux and while nitrogen is passed through it. The solvent is distilled off in vacuo and the residue is dried to constant weight in vacuo at 80°.

USE EXAMPLES

The compounds listed in Table 2 below are applied from acetone or isopropanol solution onto fabrics of polyamide-6 filaments and polyesters, using a padder, the wet pick-up being 40–50%. The amount of product is so chosen that after drying there is about 0.06% of fluorine on the fabrics. The acetone or isopropanol solutions contain about 0.6 g of substance in 250 ml.

The fabrics are air-dried, condensed for 1 minute at 160° C. and then subjected to a 3-hour treatment in water at 100°, in a washing machine (KW). The oil repellencies found after the individual finishing steps, the determinations being carried out according to the AATCC (Test Method No. 118-1966 of the American Association of Textile Colorists and Chemists), are listed in Table 2 below. In this Table, 3 means unsatisfactory, 4 means satisfactory, 5 means good oil repellency, 6 means very good oil repellency and 7 stands for outstandingly good values.

TABLE 2

| Serial No. according to Table 1 | Polyamide | | | Polyester | | |
|---|---|---|---|---|---|---|
| | air-dried | 1 minute at 160° | 3 hours KW | air-dried | 1 minute at 160° | 3 hours KW |
| (17) | 6-7 | 6 | 6-7 | 6 | 6 | 6 |
| (19) | 5 | 5 | 4-5 | 4-5 | 5 | 5 |
| (21) | 5 | 5 | 6 | 4-5 | 5 | 5 |
| (23) | 6 | 6 | 6 | 5 | 5 | 6 |
| (33) | 5 | 5-6 | 5 | | | |
| (34) | 4-5 | 4 | 5 | | | |
| (40 | | 4-5 | 4 | 5 | | 5 |
| (42) | 5-6 | 5 | 5-6 | 5 | 5 | 5 |

The examples which follow show that the compounds according to the invention can also be applied in the form of a dispersion and that this step can be combined with a dyeing process.

EXAMPLE 1

Polyamide flock, to be package-dyed, liquor ratio 1:10–1:15,
1% acid dyestuff
1-2 ml/l of 25% strength ammonia (pH 8-8.5)
3-5 ml/l of 60% strength CH$_3$COOH, pH 4.5-5.0
optionally, 0.5-1 g/l of a leveling agent based on stearylamine ethoxylate, 18-22 moles of ethylene oxide
2-5 g/l of an emulsion based on benzoxypropionitrile and
0.1-0.2% of the compound according to the invention (based on weight of goods).

Dyeing is started at 30° C. by adding ammonia, leveling agent and emulsion. The liquor is mixed for about 5 minutes, the dissolved dyestuff is introduced into the dyebath and the latter is heated to 80°0 C. bath temperature at a rate of about 1°/min. The pH is brought to 5-6 by adding 3-5 ml/l of 60% strength CH$_3$COOH, the dispersion of the compound according to the invention is added and after a mixing time of 5 minutes the batch is heated further to a dyeing temperature of 90°-120° C., preferably to 98°-110°. After about 60 minutes the dyeing is rinsed and dried. Drying at temperatures of 120°-160° for 3-5 minutes is to be preferred.

EXAMPLE 2

Polyamide flock, package system, liquor ratio 1:10–1:15
1% of acid dyestuff
1-2 ml/l of 25% strength ammonia (pH 8-8.5)
optionally 0.5-1 g/l of a leveling agent based on stearylamine ethoxylate, with 18-22 moles of ethylene oxide
3-5 ml/l of 60% strength CH$_3$COOH Dyeing is started at 30° C. by adding ammonia, leveling agent and dyestuff, and the charge is heated to 98° C. After 60 minutes the dyeing batch, which is now finished, is cooled to 80° C. and
3-5 ml/l of 60% strength acetic acid (pH 4.5-5.0)
2-5 g/l of an emulsion based on phenoxypropionitrile or benzoxypropionitrile and
0.1-0.2% of the compound according to the invention (calculated on weight of goods)

are added to the dyebath. After a mixing time of about 5 minutes, the liquor is heated again to 90°-120° C., preferably to 98°-110° C., left thereat for about 60 minutes and cooled to about 60° C.; the goods are rinsed and dried at temperatures of 120°-160° C. for 3-5 minutes.

EXAMPLE 3

Package-dyeing a polyester yarn, liquor ratio 1:8–1:12
1% of dispersion dyestuff
about 1 ml/l of 60% strength CH$_3$COOH (pH 5.2)
2 g/l of a carrier based on diphenol or o-phenylphenol and
0.1-0.2% of the compound according to the invention (calculated on weight of goods)

Dyeing is preferably started at temperatures of around 50°-60° C., acetic acid and dyestuff are added and after a mixing time of 5 minutes the liquor is heated to 80°-85° C. The carrier, in emulsified form, and the dispersion of the compound according to the invention are added to the dye liquor and the batch is mixed for about 5 minutes and heated to 130° C. After 60 minutes, the dyeing is stopped, the liquor is cooled to 80° C. and the material is rinsed and dried for 3-5 minutes at 120°-160° C.

In all three examples, the following values of the oleophobic character were measured by the 3M/AATCC method:
Compound No. (33): 100/5
Compound No. (39): 120/6

What we claim is:
1. A perfluoroalkyl ester of an anthranilic acid, of the formula (1)

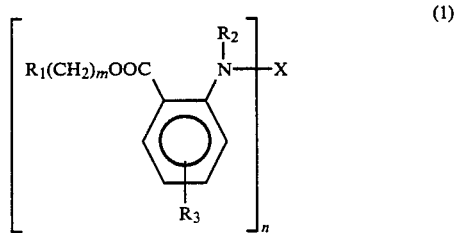

in which R$_1$ is perfluoroalkyl or perfluoroalkoxy-perfluoroalkyl, in each case having a total of 2-20 carbon atoms, R$_2$ is hydrogen, straight-chain or branched C$_1$-C$_4$-alkyl or phenyl, R$_3$ is one or more radicals selected from fluorine, chlorine, bromine, lower alkyl, lower alkoxy, carboxyl, C$_1$-C$_4$-alkanoylamino, cyano, carboxylic acid ester, carboxamide, monoalkylcarboxamide, dialkylcarboxamide, sulfo, sulfonic acid ester, sulfonamide, monoalkylsulfonamide, dialkylsulfonamide, or phenyl, m is an integer from 1 to 6, n is an integer from 1 to 3, and X, if n=1, is a group of the formula

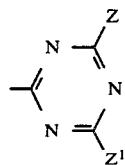

or, if n=2, is a group of the formula

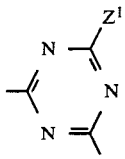

or, if n=3, is a group of the formula

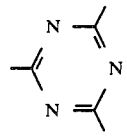

wherein, Z is chlorine, hydroxyethylamino or bis-hydroxyethylamino, and $Z^1$ is chlorine, hydroxyethylamino, bis-hydroxyethylamino, dialkylaminoalkylamino, trialkylammoniumalkylamino, sulfoethylamino, N-alkyl-N-sulfoethylamino, piperazinyl, N-hydroxyethylpiperazinyl, N-methyl-N-hydroxyethylpiperazinyl, phenylamino, sulfophenylamino, disulfophenylamino, alkylphenylamino or sulfatoethylsulfonylphenylamino.

2. A perfluoroalkyl ester of an anthranilic acid, of the formula (1) as claimed in claim 1, in which $R_1$ is a group of the formula $C_qF_{2q+1}$, a group of the formula $H(C_2F_4)_r$ or a group of the formula $(CF_3)_2CFO(CF_2)_p$, q is 6, 8, 10, 12 or 14, r is 1, 2, 3 or 4 and p is an integer from 2 to 8, $R_2$ is hydrogen, methyl, ethyl or phenyl, and $R_3$ is one or more radicals selected from chlorine, methyl, methoxy, —COOH, —COOCH$_3$, —SO$_3$H, —SO$_2$OC$_6$H$_5$, —SO$_2$NH$_2$, CN or phenyl.

3. A perfluoroalkyl ester of an anthranilic acid of the formula (1) as claimed in claim 1, wherein $R_1$ has a total of 4–14 carbon atoms.

4. A perfluoroalkyl ester as claimed in claim 3, wherein m is an integer from 1 to 4.

5. A perfluoroalkyl ester of anthranilic of the formula (1) as claimed in claim 1, wherein m is an integer from 1 to 4.

* * * * *